(12) United States Patent
Durell

(10) Patent No.: US 6,364,830 B1
(45) Date of Patent: Apr. 2, 2002

(54) VARIABLE VIEW ARTHROSCOPE

(75) Inventor: William E. Durell, N. Barrington, IL (US)

(73) Assignee: Durell & Gitelis, Inc., N. Barrington, IL (US)

(*) Notice: Subject to any disclaimer, the term of this patent is extended or adjusted under 35 U.S.C. 154(b) by 0 days.

(21) Appl. No.: 09/452,340

(22) Filed: Nov. 30, 1999

(51) Int. Cl.[7] .................................................. A61B 1/00
(52) U.S. Cl. ........................ 600/173; 600/129; 600/171
(58) Field of Search ................................ 600/129, 171, 600/173, 176; 359/851, 852, 856, 857, 862

(56) References Cited

U.S. PATENT DOCUMENTS

| | | | |
|---|---|---|---|
| 3,643,654 A | * | 2/1972 | Felbarg ..................... 600/188 |
| 3,856,000 A | | 12/1974 | Chikama |
| 3,918,438 A | * | 11/1975 | Hayamizu et al. .......... 600/173 |
| 4,140,364 A | | 2/1979 | Yamashita et al. |
| 4,697,577 A | | 10/1987 | Forkner |
| 4,723,843 A | | 2/1988 | Zobel |
| 4,838,247 A | | 6/1989 | Forkner |
| 4,846,154 A | | 7/1989 | MacAnally et al. |
| 4,858,002 A | * | 8/1989 | Zobel .......................... 358/98 |
| 4,877,314 A | * | 10/1989 | Kanamori ................... 350/422 |
| 5,184,602 A | | 2/1993 | Anapliotis et al. |
| 5,424,877 A | * | 6/1995 | Tsuyuki et al. ............. 359/663 |
| 5,603,687 A | | 2/1997 | Hori et al. |
| 5,613,936 A | | 3/1997 | Czarnek et al. |
| 5,743,846 A | * | 4/1998 | Takahashi et al. .......... 600/166 |
| 6,139,490 A | * | 10/2000 | Breidenthal et al. ........ 600/166 |

FOREIGN PATENT DOCUMENTS

| | | |
|---|---|---|
| WO | WO 95/25460 | 9/1995 |
| WO | WO 99/42028 | 8/1999 |

* cited by examiner

*Primary Examiner*—John P. Leubecker
(74) *Attorney, Agent, or Firm*—Hale and Dorr LLP

(57) ABSTRACT

A variable-view arthroscope or like instrument (endoscope, etc.) includes an elongated housing tube extending from an outer control end to an inner image input end that is closed by an input lens or window. A lighting apparatus illuminates a surgical working area beyond the image end of the housing tube. A first mirror intercepts light reflected from the surgical working area to produce a working image that is reflected to a second mirror that in turn reflects the working image to impinge upon the input end of a relay lens assembly. The working image is transmitted to a receptor, which is located near the outer (control) end of the housing tube. The relay lens applies the image to an image device, such as a conventional CCD unit, that transmits the image to a location exterior to the scope. A control varies the position of one or both of the mirrors between first and second limits.

29 Claims, 17 Drawing Sheets

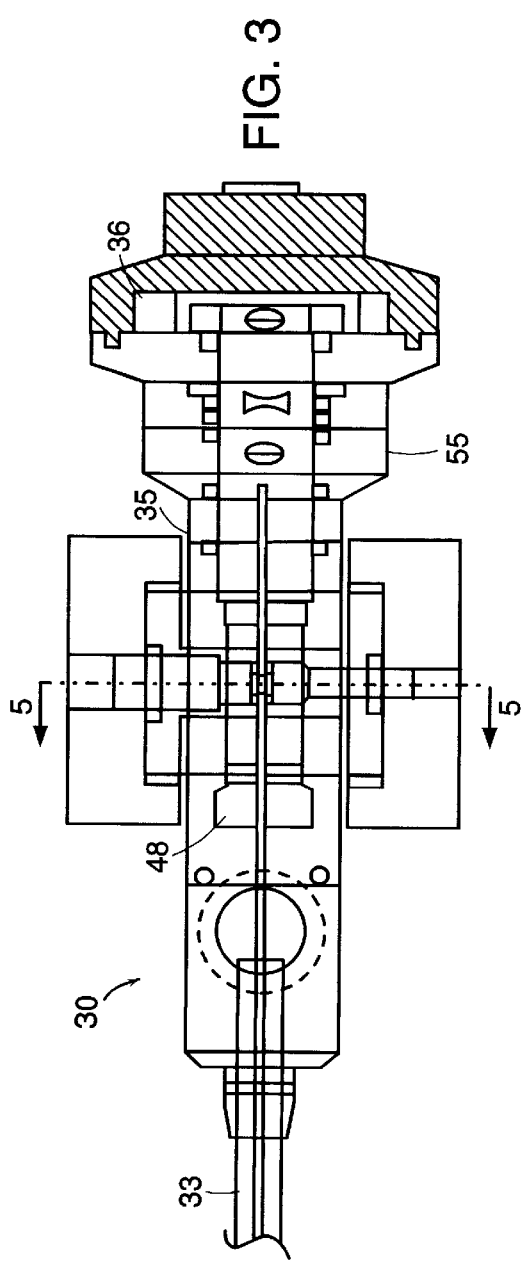
FIG. 3
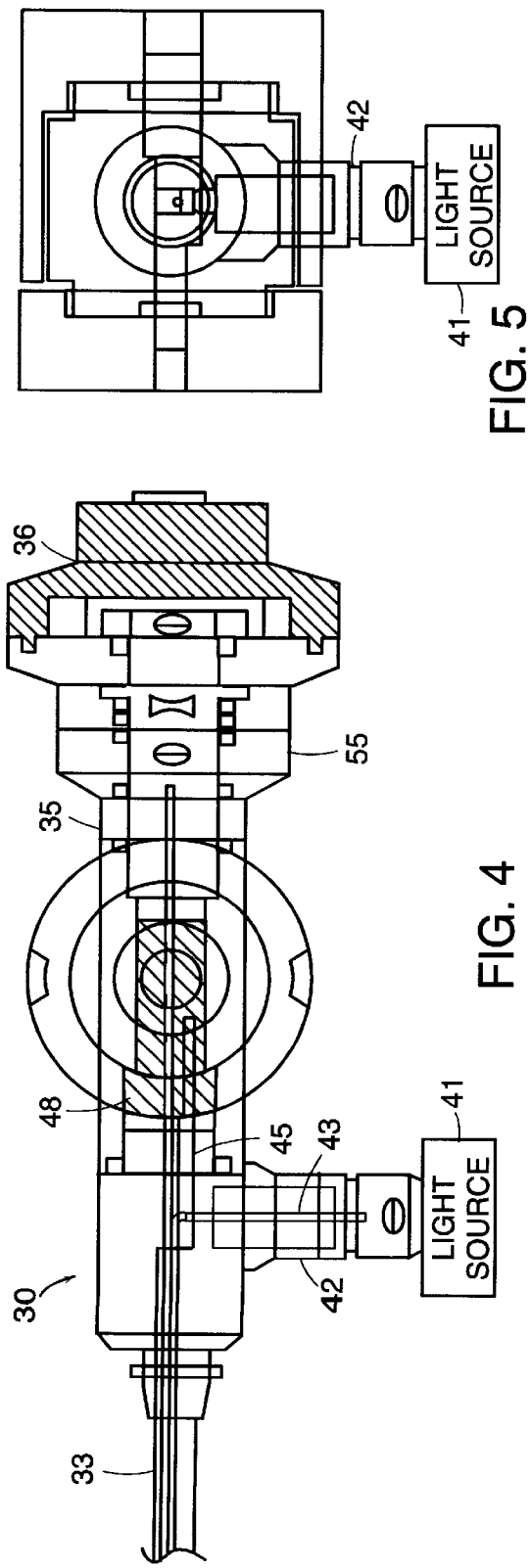
FIG. 4
FIG. 5

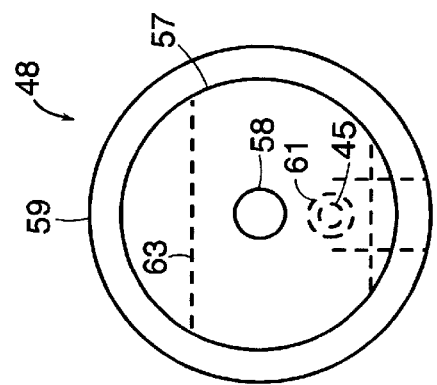
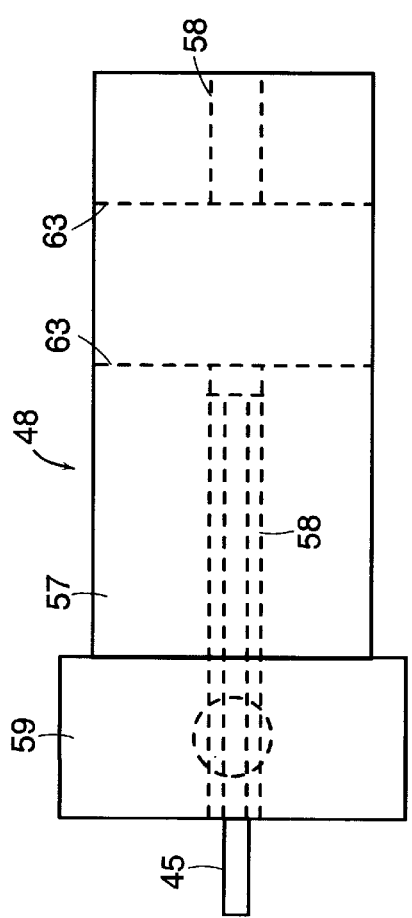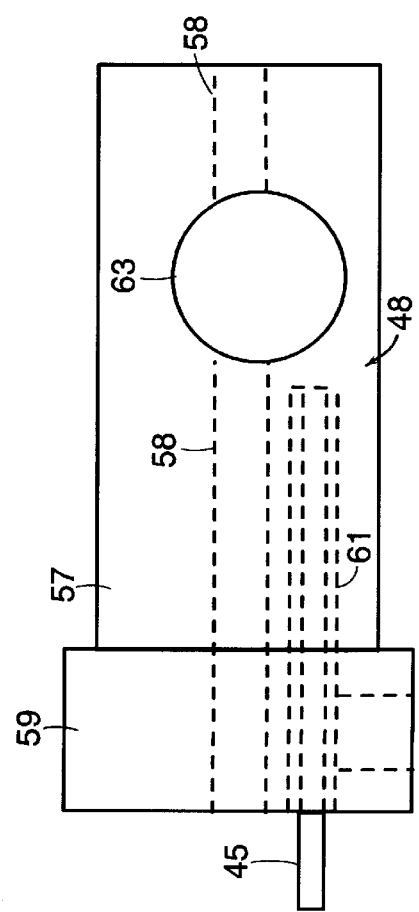

VARIABLE VIEW ARTHROSCOPE

BACKGROUND OF THE INVENTION

Arthroscopes and other like optical instruments, such as endoscopes, have long been known in the field of surgery and in other fields. In this application, the invention is described in connection with an arthroscope or similar instrument employed for surgery, as in human surgery.

Over the last fifteen or more years the nature of surgery has changed substantially, with minimally invasive surgery becoming a mainstay. Within the orthopedic community, in particular, arthroscopy and similar techniques have become the most common surgical procedures. Surgery using such techniques is less painful for the patient and, in most instances, can be performed more quickly and safely than with techniques that require greater invasion of the patient's body; anesthesia is also less complicated, the surgery can often be handled on an outpatient basis, and the procedures are more cost effective. Patients return to normal life more quickly, and hospital stays may be reduced in length or even eliminated. However, all of these benefits are available only if the minimally invasive surgery allows for better diagnostic capabilities, improved surgical techniques, and reduced iatrogenic damage. Similar benefits are available with other, non-surgical, instruments.

One problem in these minimally invasive techniques derives from limitations in the arthroscopes, endoscopes and other principal optical instruments employed. In particular, the rather limited field of view afforded by even the best instruments previously commercially available has inhibited progress to at least some extent; available instruments and techniques have not changed dramatically since 1985. A substantial improvement in the field of view available to a person employing an arthroscope or like instrument for exploratory or repair procedures is much needed.

Several techniques for modification (widening) of the view offered by arthroscopic/endoscopic instruments have been proposed, but they have not been especially successful. Generally, such proposals have required packing a plurality of movable lenses or prisms into the input end of the instrument; the resulting problems of precision of construction, precision of relative movements, space requirements, optical distortions, and elimination of undesired "ambient" light have been substantial. This is not particularly surprising; interaction between the prisms and lenses involved, along with light loss, exacerbates the problem.

There is a need for an arthroscope that affords the user a broadened effective field of view and that does not require movement of the arthroscope to vary its scope of view. One such arthroscope is disclosed in copending U.S. application Ser. No. 09/243,845, entitled "Variable View Arthroscope" and filed Feb. 3, 1999, having a common inventor with the present application. In this specification and in the appended claims the term "arthroscope" means and should be interpreted to include an endoscope or any other like optical instrument, whether used for surgery or otherwise.

SUMMARY OF THE INVENTION

The present invention relates to a variable view arthroscope comprising an elongated housing having an image input end spaced from an outer control end. Lighting is provided for illuminating a working image area beyond the image input end of the housing tube. An input lens, located in the input end of the housing tube, intercepts light reflected back from the working area. The input lens, preferably a diverging type lens, closes (and usually seals) the image input end of the housing tube, which is beveled at an angle of 30° to 60°. The reflected light constitutes a working image and the light image or object rays pass from the working area through the input lens and are directed to a movable mirror. The movable mirror may be rotatable or it may move linearly. There is a control, for example, an elongated control rod, for varying the position of the movable mirror to any position or to a series of fixed positions between a first limit position and a second limit position. A fixed mirror is positioned to intercept light reflected from the movable mirror, redirecting that light toward a relay lens assembly located near the fixed mirror position. The relay lens assembly directs the light image from the fixed mirror through the length of the relay lens assembly to impinge upon a focusing lens assembly. The focusing lens assembly includes a focusing and zoom lens and their controls, and is preferably located in the control portion of the arthroscope.

In an alternative preferred embodiment of the present invention, the input end of the arthroscope includes an input lens, a first mirror, a second mirror and a relay lens assembly. The first mirror is fixed in relation to the input lens but the two move as a unit to alter the view of the arthroscope. The second mirror is movable and directs the image into the relay lens assembly. The input lens and first mirror may rotate about the same axis as the second mirror. As object rays pass through the input lens to the first mirror, to the second mirror and into the relay lens assembly, the length of the axial ray remains the same as the angle of view of the arthroscope changes. The lengths of the rim rays may also remain the same as the angle of view of the arthroscope changes.

BRIEF DESCRIPTION OF THE DRAWINGS

FIG. 3 is a plan view, on an enlarged scale, of the control portion of the arthroscope of FIGS. 1 and 2;

FIG. 4 is an elevation view, on an enlarged scale, of the control portion of the instrument of FIGS. 1 and 2;

FIG. 5 is a detail view taken approximately as indicated by line 5—5 in FIG. 3;

FIG. 7A is an elevation view, on an enlarged scale, of a slide member used in the arthroscope of FIG. 1;

FIG. 7B is a plan view of the slide of FIG. 7A;

FIG. 7C is an end view of the slide of FIGS. 7A and 7B;

DESCRIPTION OF THE PREFERRED EMBODIMENTS

One preferred embodiment of the invention is illustrated as an arthroscope 30, shown in FIGS. 1–10.

Figure 1:
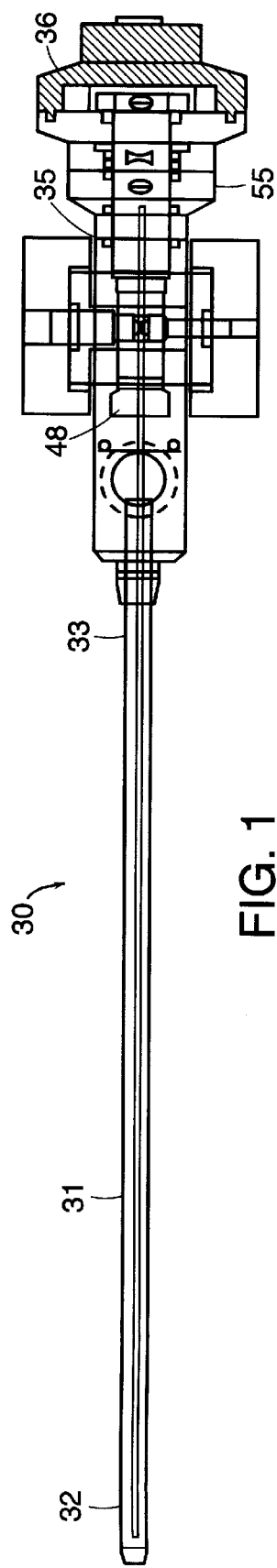
FIG. 1 is a plan view of a variable view arthroscope constructed in accordance with a preferred embodiment of the invention.
Figure 2:
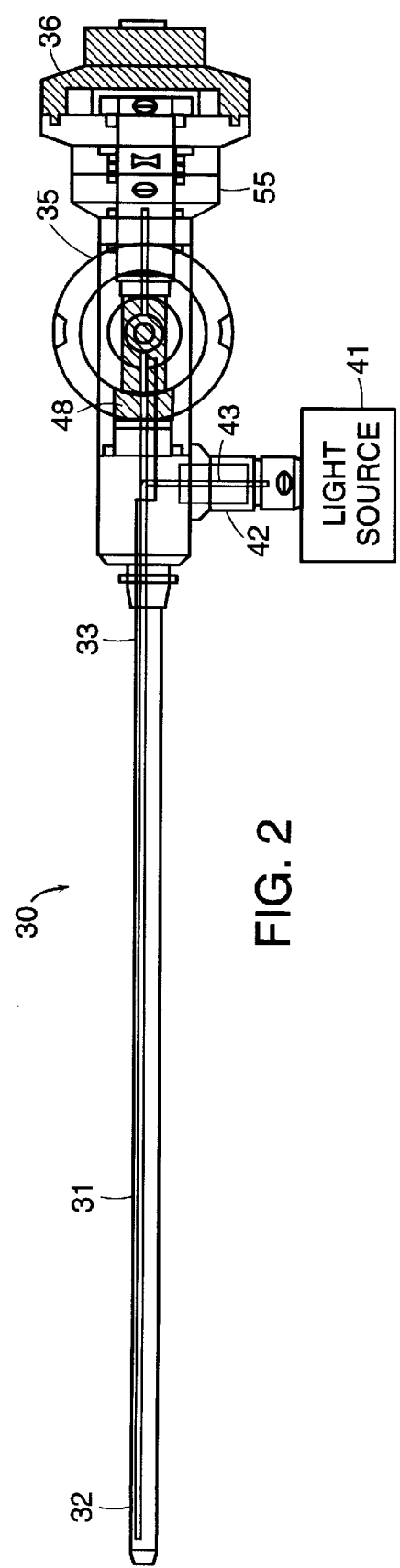
FIG. 2 is an elevation view of the instrument of FIG. 1.

As shown in FIGS. 1 and 2, arthroscope 30 includes an elongated housing tube 31, which has an image input end 32 and a control end 33. Housing tube 31, and more specifically its control end 33, may extend into the outer control portion 35 of arthroscope 30, shown in greater detail in FIGS. 3–5.

As shown in FIGS. 1–4, the control portion 35, from which the control end 33 of the housing tube 31 of arthroscope 30 projects, ends with a CCD attachment 36. The CCD attachment 36 is connected by appropriate means to an image screen (not shown) to be viewed by a person using arthroscope 30. CD attachment 36 may be of conventional construction, does not constitute a part of the present invention, and is not shown in detail.

Figure 6D:
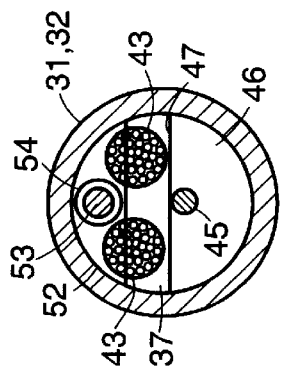
FIG. 6D is a sectional view taken approximately along line 6D—6D in FIG. 6A.
Figure 6C:
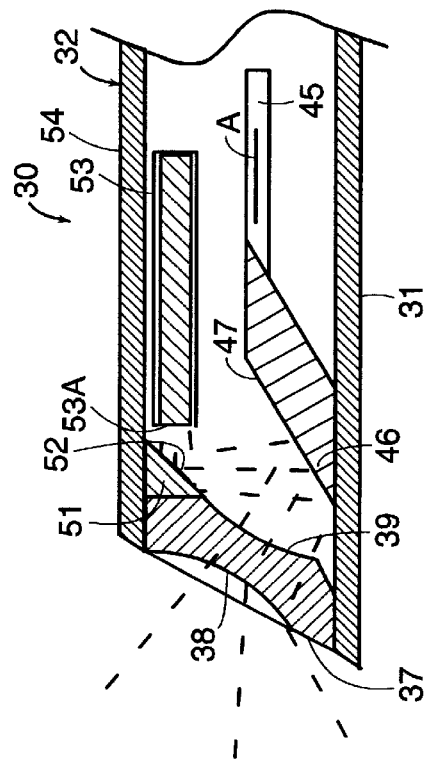
FIG. 6C is a sectional elevation view, like FIGS. 6A and 6B, of the image input end of the arthroscope of FIG. 1, adjusted for a maximum downward view.
Figure 6A:
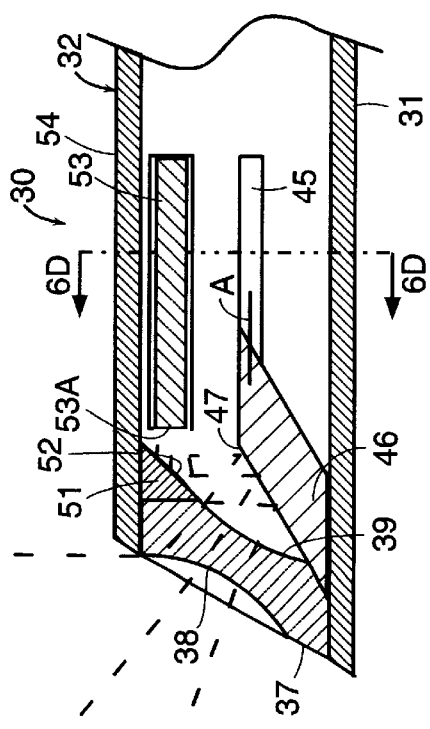
FIG. 6A is a sectional, longitudinal elevation view, on an enlarged scale, of the image input end of the arthroscope of FIG. 1, adjusted for a maximum upward view.
Figure 6B:
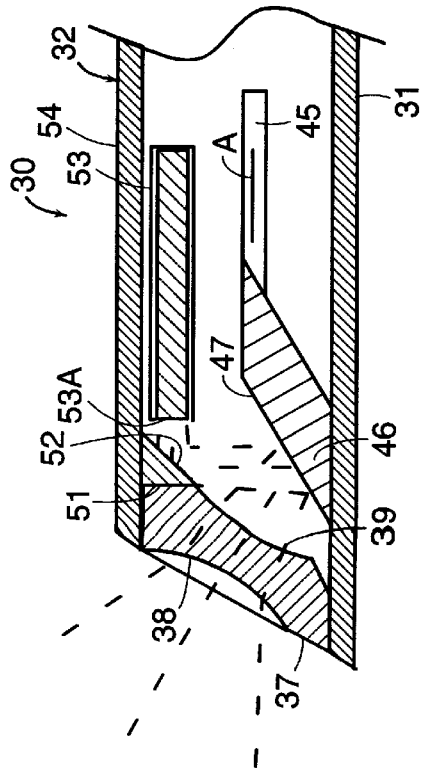
FIG. 6B is a sectional elevation view, like FIG. 6A, of the image input end of the arthroscope of FIG. 1, adjusted for an intermediate view.

As best shown in FIG. 2 and in the enlarged views of FIGS. 6A–6C, the image input end 32 of housing tube 31 is beveled at its extreme end; the bevel is usually between 30° and 60°. The outer end of housing tube 31, shown in enlargement in FIGS. 6A–6C, is closed by a diverging input lens 37 (plural lenses may be used). Input lens 37 has an outer concave surface 38 spaced from an inner concave surface 39. Input lens 37 is preferably sealed into the tip of the input end 32 of housing tube 31; a suitable seal material to mount lens 37 in place in the end of housing tube 31 is any conventional sealing adhesive approved by the FDA for in vivo use. Input lens (or lenses) 37 may be formed of optical glass or any other suitable lens material. When a single input lens is used, input lens 37 preferably has a rim matched as closely as possible to the inside diameter of the housing tube 31 at its image input end 32 to assure a good seal between the housing tube and the input lens. Similar expedients should be employed if plural input lenses are utilized.

Arthroscope 30 includes, at the opposite end of tube 31, an outer control portion 35 and a light source 41 that is connected to a lighting assembly 42; see FIGS. 2 and 4. The lighting assembly 42 includes one or more optic fiber bundles 43; the fiber optic bundle (or bundles) extend to the input end of the arthroscope; see FIGS. 4 and 6D. For clarity, the optic fiber bundles 43 have been omitted in FIGS. 6A–6C. The lighting assembly 42 illuminates a surgical working area (not indicated) beyond the image input end 32 of the housing tube; typically, illumination of the surgical working area is through the input lens 37.

A control, shown in FIG. 4 as a control rod 45, extends longitudinally through the housing tube 31 from outer control portion 35 to its input end 32. Rod 45 is used to vary the position of a slidably movable mirror 47 (See arrows A in FIGS. 6A–6C) along the axis of rod 45. Mirror surface 47 is shown as planar in the drawings, but the movable mirror may be concave or other shapes. The mirror surface 47 is aligned with but spaced from the inner surface 39 of input lens 37. See FIGS. 6A–6C. The end of control rod 45 is affixed to the movable mirror 47 at its base 46, as best shown in the enlarged views of FIGS. 6A–6C. A suitable commercially available adhesive may be used to join the end of rod 45 to the base 46 of the movable mirror 47; alternatively, soldering or brazing may be used if desired. The tip of control rod 45 may be polished and coated to afford a suitable movable mirror, eliminating the need for a separate part such as base 46.

At the control end 35 of the arthroscope 30 the control rod 45 extends into and engages a slide 48. Slide 48 is driven linearly by two control knobs 49 and 50, as described hereinafter in connection with FIGS. 9A–9C.

In the arthroscope 30, as shown in FIGS. 6A–6C, the base 46 of the movable mirror 47 slides linearly between a maximum upward view position (FIG. 6A), through an intermediate position (FIG. 6B), to a maximum downward view position (FIG. 6C). The movement of the movable mirror base 46 may be reversed, moving from its maximum downward position (FIG. 6C) toward its maximum upward position (FIG. 6A). The images that may be provided to a surgeon by the arthroscope 30 overlap. The maximum upward view of FIG. 6A, with movable mirror 47 advanced by control rod 45 to a position immediately adjacent input lens 37, has an overlap of about fifty percent with the maximum downward view (FIG. 6C) afforded when the sliding mirror 47 is fully retracted.

At the top of the input end of arthroscope 30, as seen in FIGS. 6A–6C, there is a fixed mirror 52 mounted on a base 51. The fixed mirror 52 intercepts object rays from the movable mirror surface 47 and re-directs those rays to impinge upon the input end 53A of a relay lens assembly 53. Relay lens assembly 53, FIGS. 6A–6C, may be of conventional construction having an outer stainless sleeve 54 for stability and directs the light toward a receptor, shown as a focusing lens assembly 55 (FIGS. 1, 2, 3 and 4). The focusing lens assembly 55 consists of focusing and zoom lenses and is of conventional design. The focusing lens assembly 55 directs the light image in the customary manner, into the CCD attachment 36; see FIGS. 1–4. A slide 48 is located in the control portion 35 of arthroscope 30; the slide, shown in FIGS. 7A–7C, comprises a main body 57 having an axial relay lens opening 58; the relay lens opening 58 also extends through an enlarged end 59 of the slide. A socket 61 also in slide 48, formed to align and attach control rod 45 to slide 48, is shown in FIG. 7B. In the illustrated embodiment, the control rod socket 61 is located directly below the axial opening 58 for the relay lens.

Figure 8A:
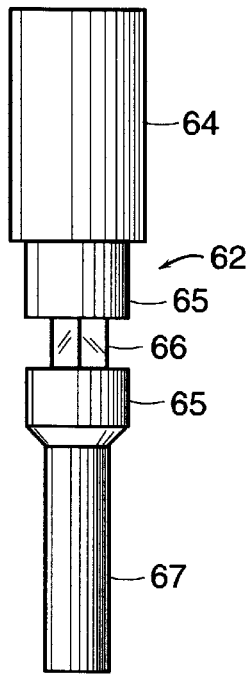
FIG. 8A is a plan view, on an enlarged scale, of a cam/axle member used in the control end (FIG. 3) of the arthroscope of FIG. 1.
Figure 8B:
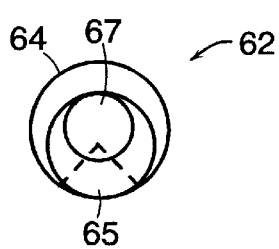
FIG. 8B is an end view of the cam/axle member of FIG. 8A.
Figure 8C:
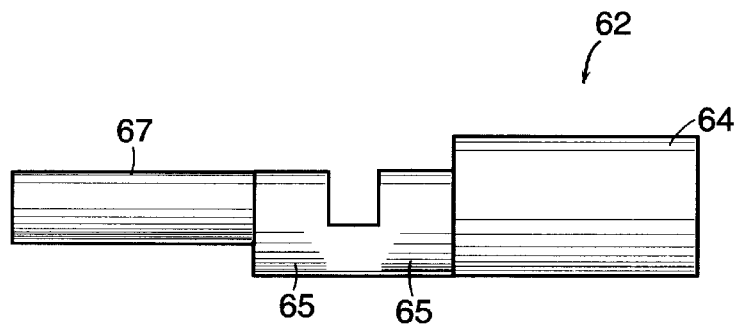
FIG. 8C is an elevation view of the cam/axle member of FIG. 8A.
Figure 9A:
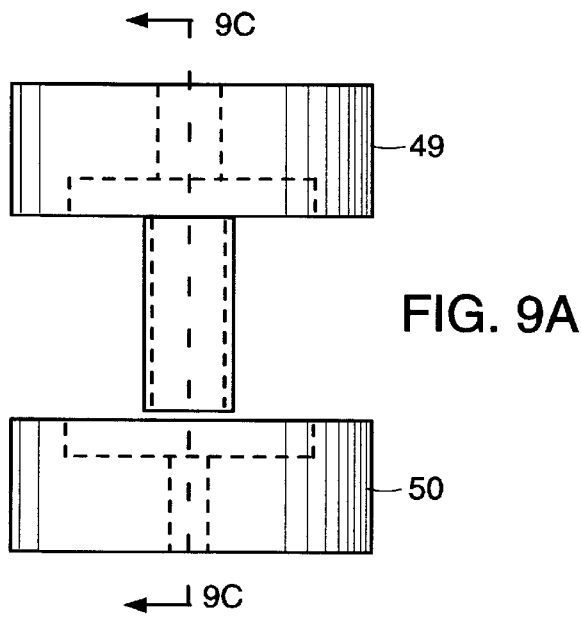
FIG. 9A is a plan view, on an enlarged scale, of two control knobs from the control end (FIG. 3) of the arthroscope of FIG. 1.
Figures 9B, 9C:
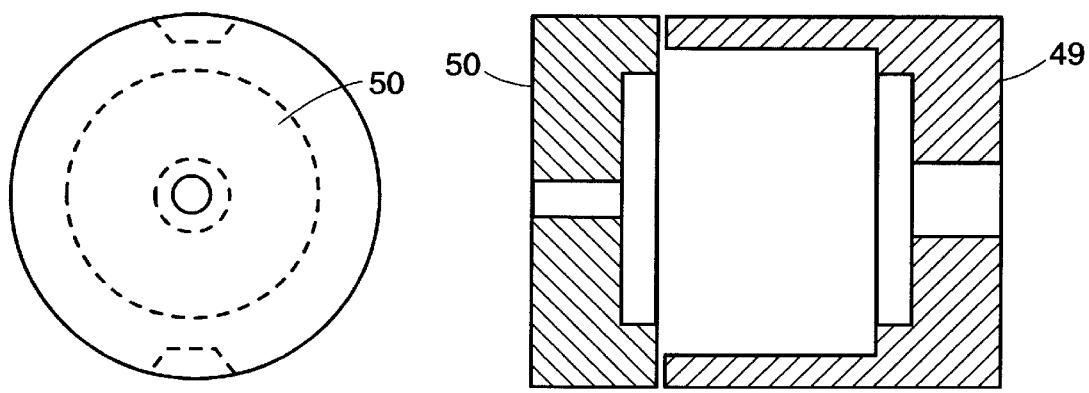
FIG. 9B is an end view of the control knobs of FIG. 9A.
FIG. 9C is a section view, taken approximately along line 9C—9C in FIG. 9A, of the control knobs.

The cam portion 65 of cam/axle member 62 is positioned in a central transverse opening 63 in slide 48; see FIGS. 7A–7C for opening 63, FIGS. 8A–8C for cam/axle member 62. Opening 63 is not quite circular in cross-section; it is enlarged or "stretched" slightly, as is most apparent in FIG. 7B. The cam/axle member 62 includes a large control knob shaft attachment segment 64 of circular cross-section, cam segment 65 contains a relay lens assembly slot 66, and a small control knob shaft attachment segment 67. This preferred construction is shown in detail in FIGS. 8A–8C. Two control knobs, shown in FIGS. 9A–9C, are mounted on the outer ends 64 and 67 of cam/axle member 62 (FIGS. 8A–8C). The control knobs include a right-hand control knob 49 that is fitted onto the large control wheel shaft attachment segment 64 of the cam/axle member 62. The second or left-hand control knob 50 fits onto the smaller control knob shaft attachment segment 67 of cam/axle member 62. See FIGS. 8A–8C and 9A–9C.

The control knobs 49 and 50 and their shaft attachments 64 and 67, respectively, may be connected to each other by conventional means. Either of the control knobs 49 and 50 can be used to rotate cam 65 within slide opening 63, thus causing slide 48 and the attached control rod 45 to move linearly in relation to the rotational motion of cam/axle 62.

Figure 10:
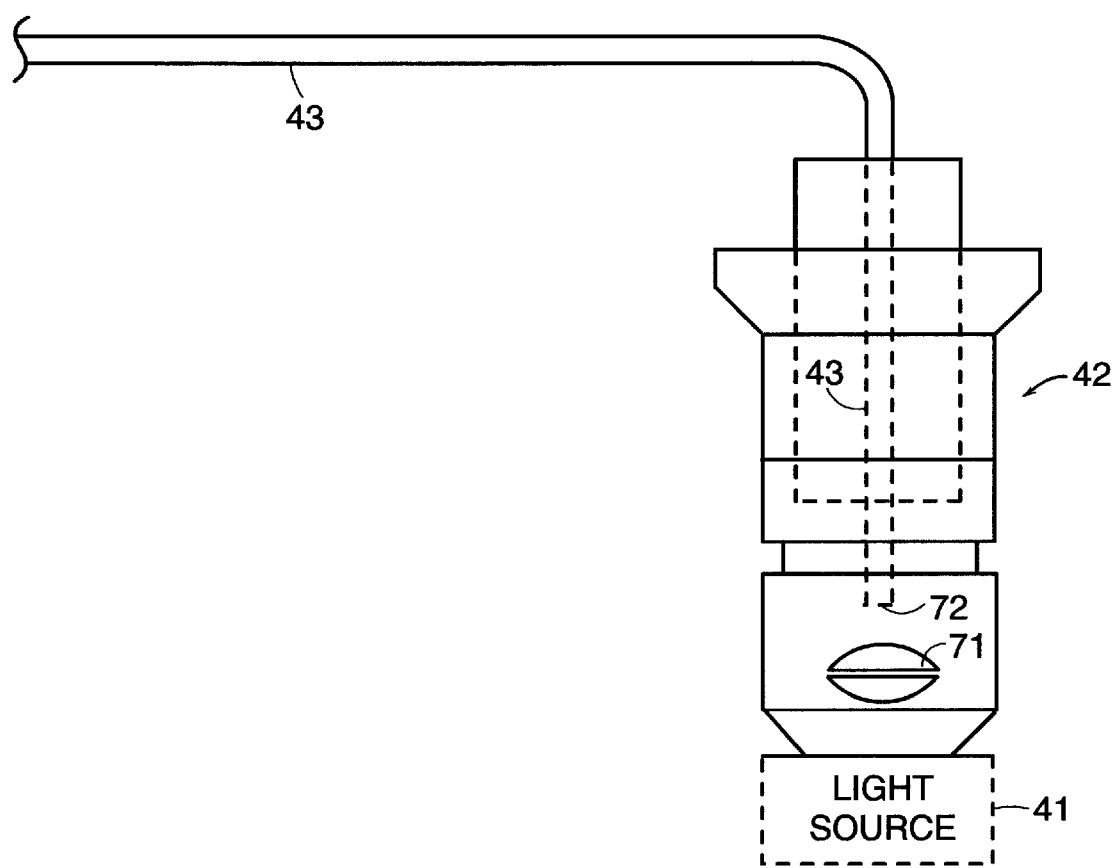
FIG. 10 is an elevation view, on an enlarged scale, of the lighting apparatus for the arthroscope of FIG. 1.

The lighting assembly 42, illustrated in FIG. 2 and shown in greater detail in FIG. 10, may include a condenser lens 71 to focus light from a suitable source 41 onto one end 72 of the light bundles 43 that extend to the input end of the arthroscope 30. See FIG. 6D. Two or more fiber optic light bundles 43 may be provided to supply light to the input end of arthroscope 30. As previously noted, the lighting assembly shown is conventional in construction and has been described only generally.

Operation of the arthroscope 30 (FIGS. 1–10) can now be considered. At the outset, light from source 41 (FIG. 2) is focused upon the end 72 of one or more fiber optic bundles 43. Light passes through the fibers 43 and illuminates a surgical working area just beyond the input end 32 of the arthroscope 30 (FIGS. 1 and 2). In arthroscope 30, light passes into bundle(s) 43 and reflects, at least in part, from the fixed mirror 52 onto the reflective surface of the movable mirror 47, and then passes through the input lens 37 into the area to he illuminated.

Light reflected from the surgical working area forms an image of object rays after passing through input lens 37 and impinges on the movable mirror 47. The image is directed from the movable mirror 47 to impinge upon the fixed mirror 52. From the fixed mirror 52 the light image is re-directed toward the input end 53A of the relay lens assembly 53; see FIGS. 6A–6D. The relay lens system 53 supplies the image to the CCD attachment 36, through focusing lens assembly 55, to be viewed by the surgeon or other person using the arthroscope 30.

If the person using arthroscope 30 is dissatisfied with the image available through the CCD attachment 36, control knobs 49 and/or 50 may be used to provide an image of a different portion of the surgical region. As shown, the control knobs, through cam/axle member 62 (FIGS. 8A–8C), slide 48 (FIGS. 7A–7C), and rod 45 (FIGS. 6A–6C) can advance the movable mirror 47 toward the input lens 37 (see FIG. 6A), or retract the movable mirror 47 from the input lens 37 (see arrow A in FIGS. 6B and 6C) to a "lower" position. In this way the image supplied to the surgeon or other person using the instrument 30 can be and is varied to a substantial extent with no change in the position of the instrument. In effect, the overall viewing range of the instrument 30 is enhanced by at least thirty degrees with no need to reposition the instrument axially. Further alteration or correction of the image can be afforded by appropriate software.

Figure 11A:
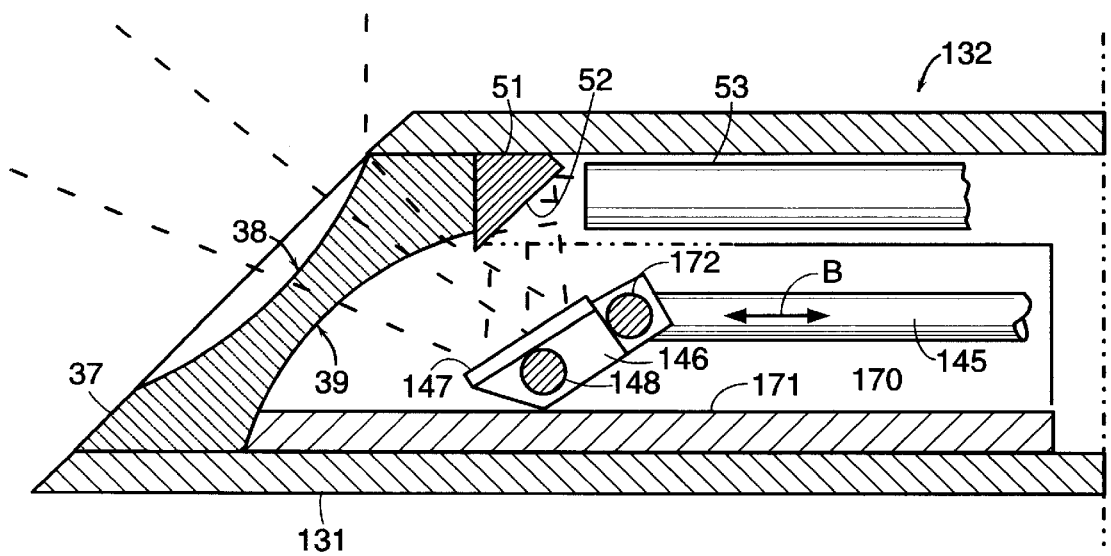
FIG. 11A is a longitudinal sectional elevation view, like FIG. 6A, of the input (viewing) end of an arthroscope comprising another embodiment of the invention, adjusted for a maximum upward view.
Figure 11B:
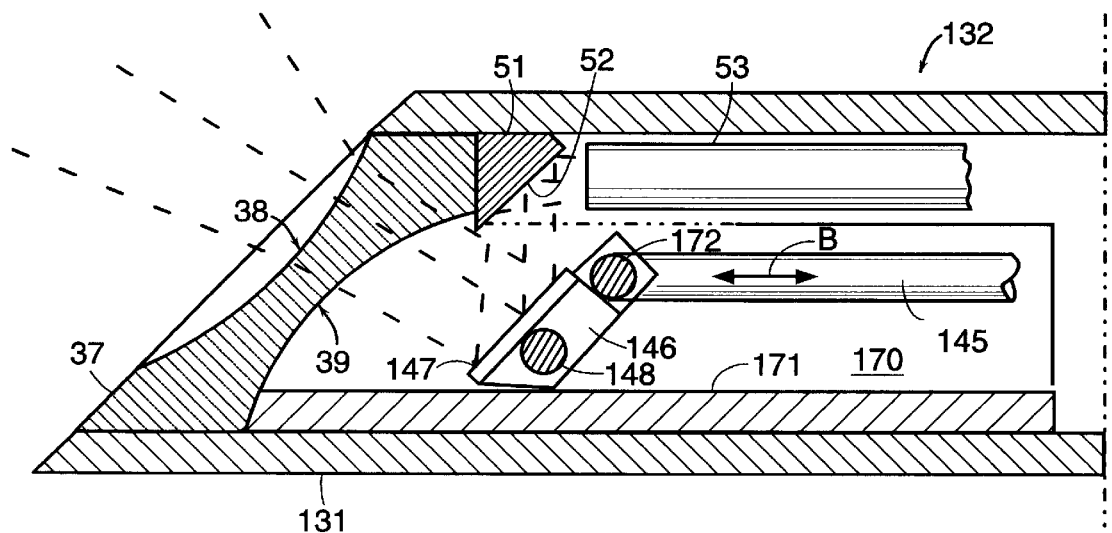
FIG. 11B is a sectional elevation view, like FIG. 11A, of the apparatus of FIG. 11A adjusted for an intermediate view.
Figure 11C:
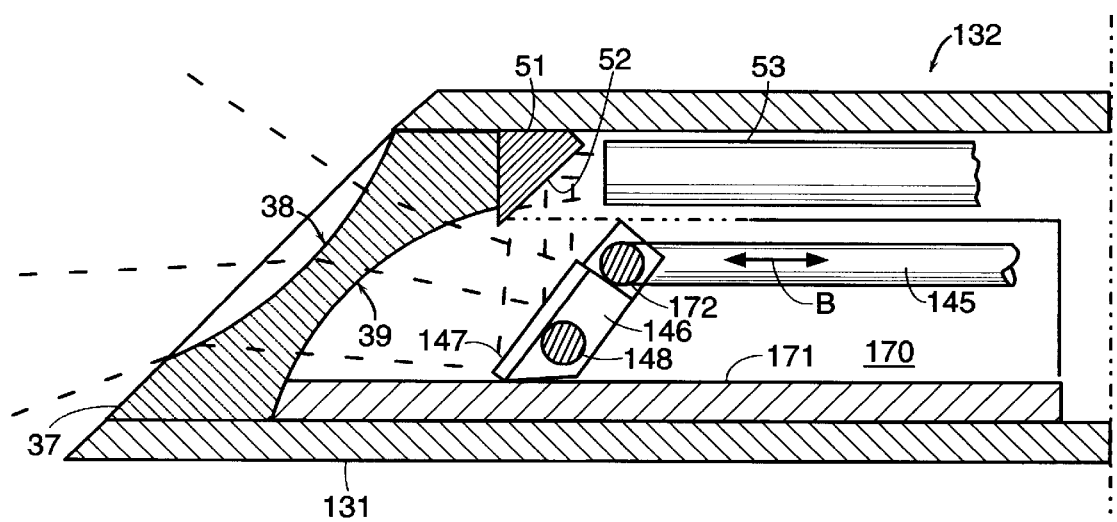
FIG. 11C is a sectional elevation view, like FIG. 11A, adjusted for a maximum downward view.

FIGS. 11A, 11B and 11C afford sectional elevation views of the input end 132 of a modified instrument and FIGS. 11A, 11B and 11C correspond to FIGS. 6A, 6B and 6C, respectively. In FIGS. 11A–11C, the reference numerals and illustrated elements correspond to those employed in FIGS. 6A–6C, except for those elements that have been modified. The instrument input end 132 of a housing tube 131 is bevelled, as previously described, and is closed by an input lens 37. The input lens 37 may have two concave lens surfaces, an outer surface 38 and an inner surface 39 as shown; other input lens structures may be used. A fixed mirror 52 is mounted in the upper portion of housing tube 31, immediately adjacent input lens 37; the fixed mirror 52 has a reflective coating, on a base 51, that faces the input end 53A of a relay lens assembly 53.

In the modification shown in FIG. IIA, there is a pivotally movable mirror 147 on a base 146. The mirror base 146 is pivotally mounted on a shaft 148 that extends transversely of the instrument between the two sides 170 (only one shown) of a generally U-shaped support member 171 positioned in the lower part of housing tube 131. The movable mirror base 146 is connected to the end of a control rod 145, as by a pin 172; rod 145 is similar to rod 45. The control rod 145 can be moved linearly as indicated by arrow B in FIGS. 11A, B and C.

The views of FIG. 11B and FIG. 11C are the same as FIG. 11A except that FIG. 11B shows the pivotally movable mirror 147 at an intermediate position, for an intermediate image, and FIG. 11C shows the pivotally movable mirror 147 positioned for a maximum "downward" view. For this description, FIGS. 11A–11C are assumed to be vertically oriented, but they could equally well be horizontally oriented, as could FIGS. 6A–6C, so that references to "upward" and "downward" could equally well be modified to "right" and "left", or vice versa.

Several parts of instrument 30 can be modified from those illustrated without appreciable effect on overall operation of instrument 30. For example, input lens 37, the shape of the movable mirrors and bases 46, 47, 146, 147 and the illustrated relay lens assembly 53 can be changed, as can the lighting assembly 42, 43. The control rod 45 (or rod 145) also may be modified; control rod 45 constitutes a preferred mechanism for operating the movable mirror 47 but any mechanism that will move the mirror 47, whether linearly or along a pivotal or other required path, can be used. The angle of the level of the outer end of housing tube 31 may be varied as desired; a level of 30° to 60° is preferred, but may depend on the primary use for instrument 30. It will be recognized that use of a CCD unit for a display is not essential. The "software" used for the display may vary appreciably. Any preferred technique to enable the instrument user to move the movable mirror over its operational range is acceptable.

An alternative embodiment of the input end of a variable view arthroscope 30' in accordance with the present invention is shown in FIGS. 12A–16. For clarity, only input end 100 of arthroscope 30' is illustrated in full. Although shown as an arthroscope providing up-down view variability, a similar configuration of arthroscope 30' could be oriented so as to provide side-to-side view variability or view variability along any other axis. The input end of the variable view arthroscope 30' in accordance with this embodiment of the present invention is indicated generally at 100. The input end 100 generally captures a light image, formed of object rays, and sends the image to the control end. As discussed herein, the object rays include an axial ray at the optical center of the object image, and rim rays at the outer edges or rims of the object image.

Figure 12A:
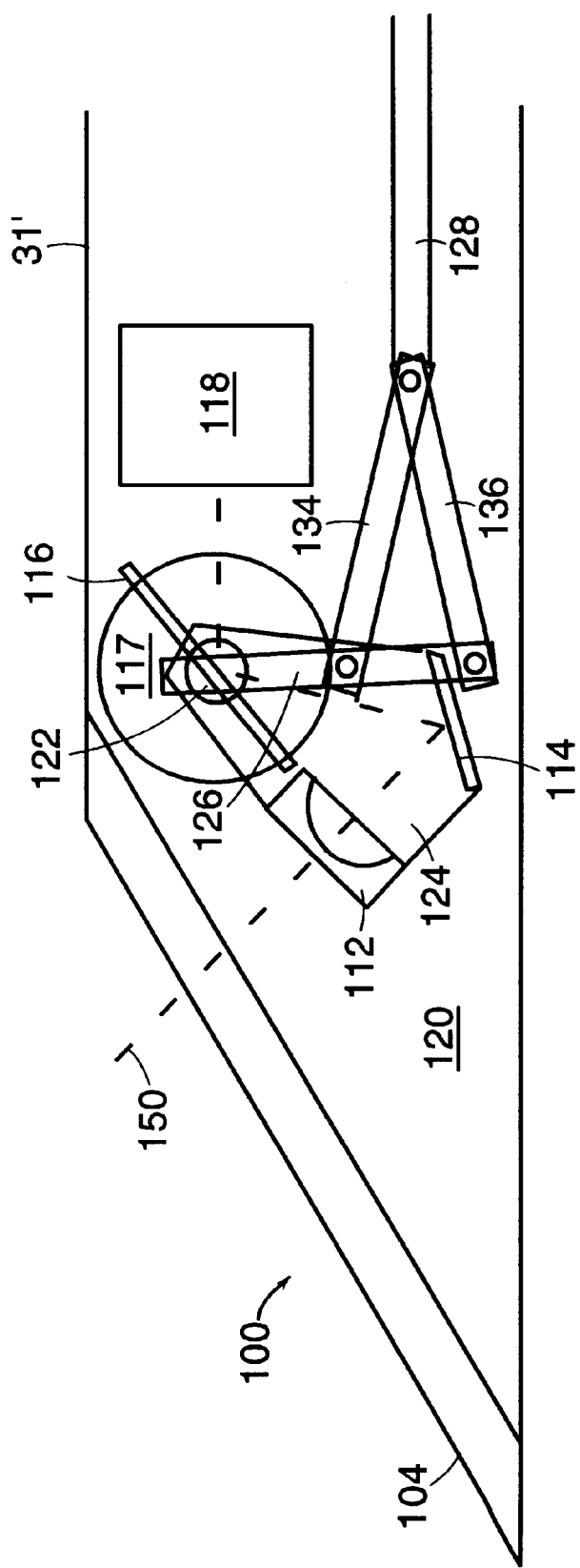
FIG. 12A is a sectional elevation view of the input end of a variable view arthroscope, adjusted for a middle view, in accordance with another embodiment of the present invention.
Figure 12B:
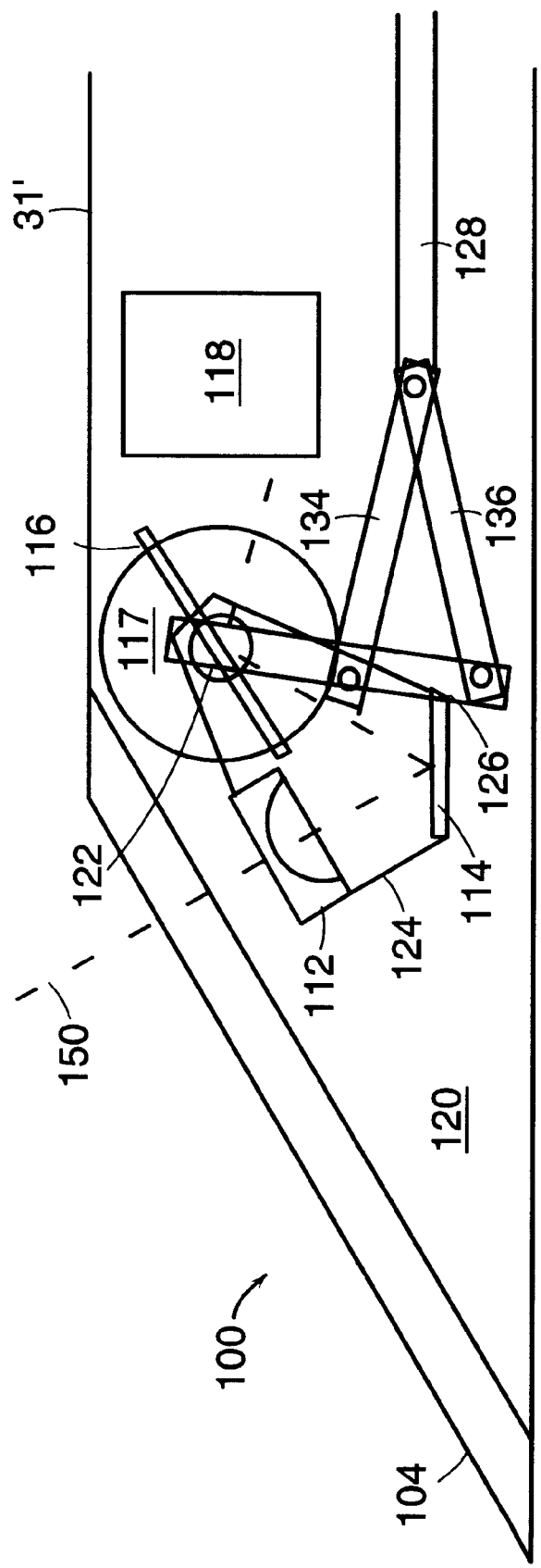
FIG. 12B is a sectional elevation view of the input end of a variable view arthroscope, adjusted for a maximum upward view, in accordance with an embodiment of the present invention.
Figure 12C:
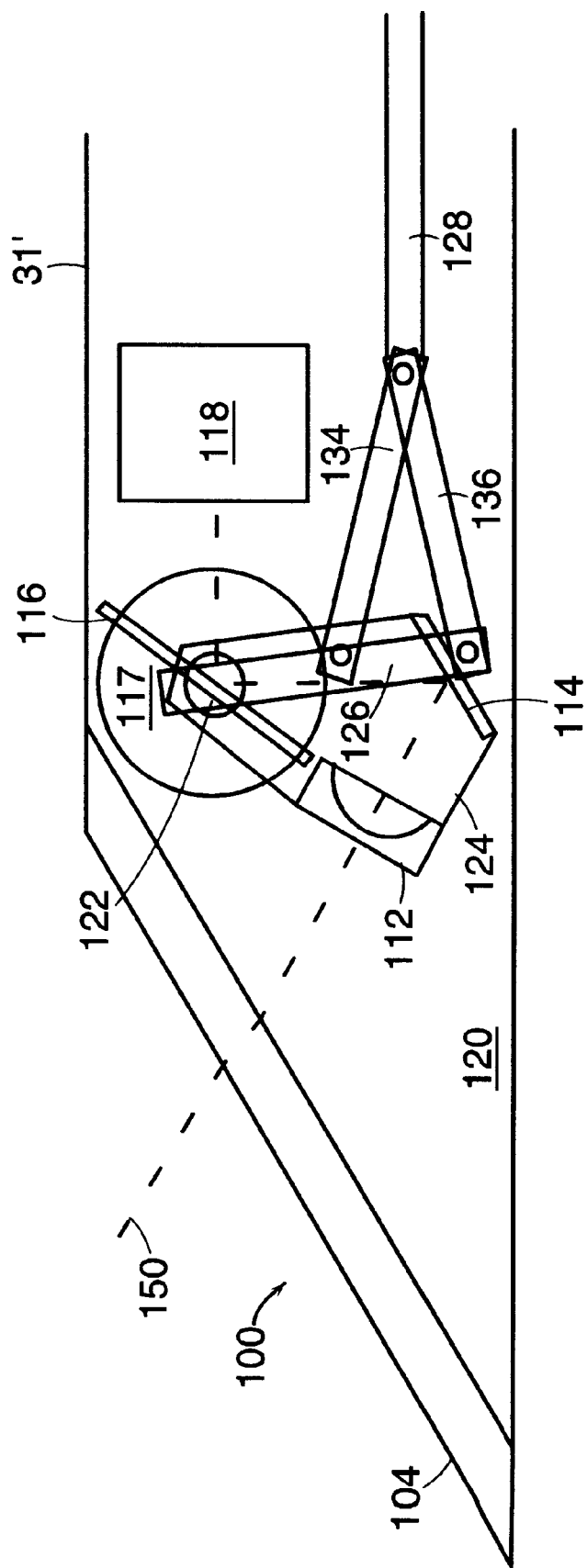
FIG. 12C is a sectional elevation view of the input end of a variable view arthroscope, adjusted for a maximum downward view, in accordance with an embodiment of the present invention.
Figure 13:
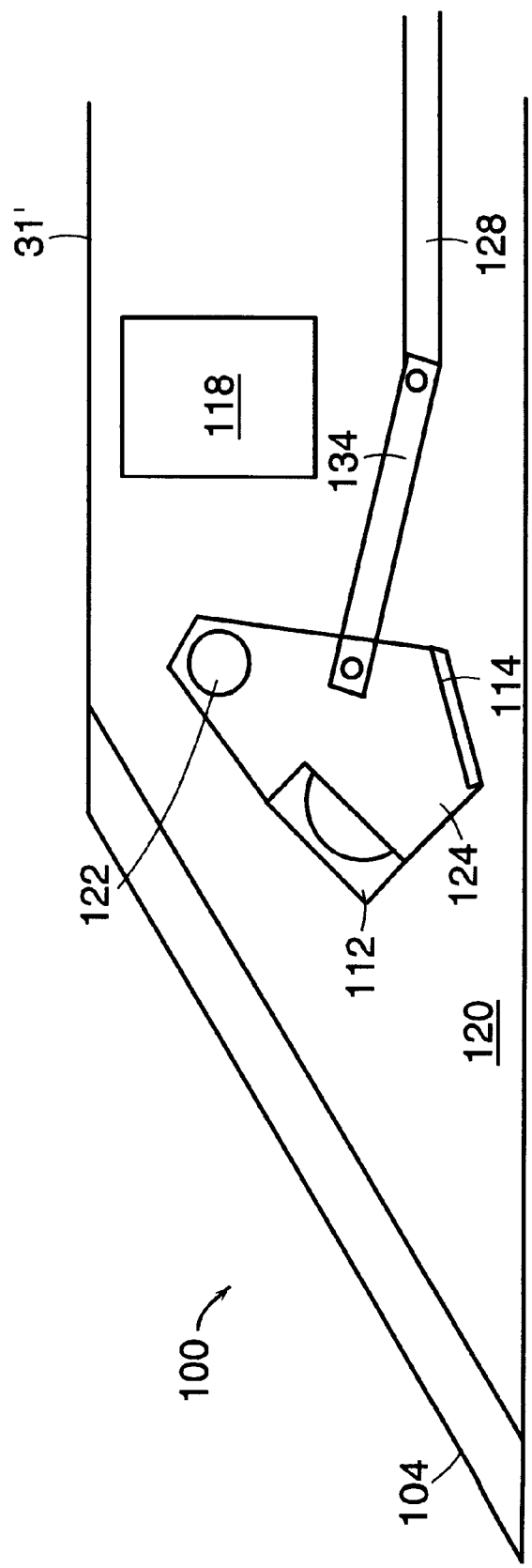
FIG. 13 is a sectional elevation view of the input end of a variable view arthroscope, adjusted for a middle view, showing the input lens assembly and associated mechanism, in accordance with an embodiment of the present invention.

As shown in FIG. 12A, the input end 100 of the arthroscope 30' is contained within an elongated housing tube 31' that extends along a central, longitudinal axis. The end of the housing tube 31' is closed by a window 104 that is fixed in place, such as by adhesive, and also may be sealed to form a sealed closure for the end of the housing tube 31'. The window 104 forms part of the sealing system for the arthroscope 30'. The window 104 may be placed so that it forms any desired angle for the closure of the end of the housing tube 31'; for example, the window maybe be placed to bevel the closure of the housing tube 31' by between about 30 and 60 degrees. Window 104 may be flat glass or other suitable material, or it may have curved surfaces; for example, window 104 may be a meniscus lens, placed to curved outward from the end of the housing tube 31'. Preferably, the end of the housing tube 31' should be formed so that the edges of the housing tube 31' are flush with the outer surface of the window 104 when the window 104 is placed at the desired angle.

The input end 100 of the variable view arthroscope 30' includes an input lens 112, a first mirror 114, and a second mirror 116. The input lens 112 is placed proximate to the window 104 and is preferably an image expanding negative lens. The input lens 112 and the first mirror 114 are fixed in relation to each other, i.e., their relative positions, including the distance and the angle between them, do not vary; and typically they are oblique with respect to each other. The input lens 112 and first mirror 114 are, however, movable and move as a unit if mounted together. In the embodiment shown in FIGS. 12A–C, the input lens 112 and the first mirror 114 are mounted on, and fixed to, a swing arm 124. Preferably they are mounted so that the plane of the surface of the first mirror 114 is at an angle of about 30 degrees from the plane perpendicular to the optical axis of the input lens 112. When swing arm 124 moves, the input lens 112 and the first mirror 114 move as a unit on the swing arm 124 and preferably rotate around an axle 122. The input lens 112, the first mirror 114 and the swing arm 124 form the input lens assembly 120. The input lens assembly 120 captures object rays from the selected viewing positions. The movement of the input lens assembly 120 allows the viewing position of the arthroscope 30', and thus the particular input image captured in the arthroscope 30', to be variable. Although in the illustrated embodiment the mounting functions as the arm that allows movement of the input lens assembly 120, these functions may also be provided separately; e.g., the input lens mounting may be separate from the first mirror mounting.

Figures 14A, 14B:
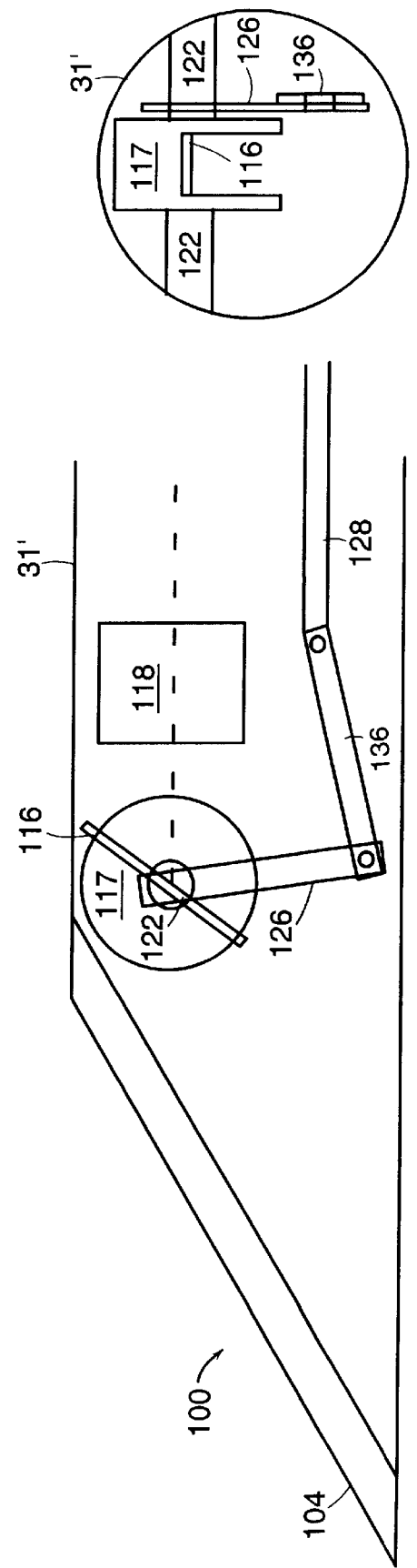
FIG. 14A is a sectional elevation view of the input end of a variable view arthroscope, adjusted for a middle view, showing the second mirror and associated mechanism, in accordance with an embodiment of the present invention.
FIG. 14B is a sectional end view of the second mirror, second mirror housing, axle, and second mirror associated mechanism in accordance with an embodiment of the present invention.

The second mirror 116 is rotatable, and preferably also rotates around the axle 122. The second mirror 116 receives the objects rays of the image captured and reflected from the input lens assembly 120, and reflects these rays to the lens relay system 118, from where they are sent to the control end of the arthroscope 30'. The second mirror 116 preferably is a top or first-surface reflecting mirror. Referring to FIG. 14B, the second mirror 116 is supported by housing 117 and suspended by axle 122. Preferably, the center of the axle 122 and the reflecting surface of the second mirror 116 are substantially coplanar. Preferably, axle 122, second mirror housing 117, and swing arm 126 operate as one unit that rotates around axle 122. In a preferred embodiment, the second mirror housing 117 and the axle 122 are formed as one unit, with the housing 117 supported on the axle 122. The middle section of the axle 122 may be machined to reduce the thickness of the axle and allow for proper positioning of the second mirror 116. The distance from the portion of the housing 117 that will support the mirror to the center of the axle 122 is the thickness of the second mirror 116. When the second mirror 116 is mounted, the reflecting surface of the second mirror 116 is at the center of the axle 122. To maintain the structural integrity of the axle 122, the axle 122 and housing 117 are preferably machined from a substantially cylindrical blank with a thicker center portion. A slot that forms the housing 117 for the second mirror is formed in the thicker center portion, leaving a sidewall for strength.

The rotation of the input lens assembly 120 provides variability in the view of the arthroscope 30'. The input lens assembly 120 rotates around an axis that is parallel to the axis around which the second mirror 116 rotates. In the illustrated embodiment, the input lens assembly 120 preferably rotates around the axle 122 that is located at the center of and extends along the plane of the surface of the second mirror 116; i.e., the first and second mirrors 114, 116 rotate around the same axis. Preferably, the input lens assembly 120 will rotate approximately 30 degrees between the most upward-facing view ("full-up") and the most downward facing view ("full-down") although a different range may be selected as desired. In a preferred embodiment, the arthroscope 30' has a total viewing range of about or greater than 100 degrees. Preferably the middle view of the arthroscope 30', i.e., the view in the middle off the range of the arthroscope 30', is at an angle 45 degrees up from the longitudinal axis of the housing tube 31' of the arthroscope 30' (as shown in FIG. 12A).

As the input lens assembly 120 rotates to different angles, it will capture object rays of different views of the object. Input object rays are to be sent from input end 100 to the control end of the arthroscope 30', typically via lens relay system 118. The object rays should be properly oriented with respect to the lens relay system 118 for improved transmission. The second mirror 116 directs the objects rays for relay to the control end of the arthroscope 30'. The view of the object that is reflected from the first mirror 114 up to the second mirror 116 should preferably then be reflected from the second mirror 116 so that the center line or axial ray of the reflected image is coaxial with the center line of the lens relay system 118. Typically, the center line of the lens relay system 118 is parallel to the longitudinal axis of the housing tube 31'. At the middle view of the arthroscope 30', at 45 degrees up from the longitudinal axis of the housing tube 31' in accordance with a preferred embodiment of this invention, the plane of the surface of the second mirror 116 is at an angle of approximately 22.5 degrees from the plane of the surface of the first mirror 114 to provide the proper orientation of the object rays into the lens relay system 118 from the second mirror 116.

Figure 16:
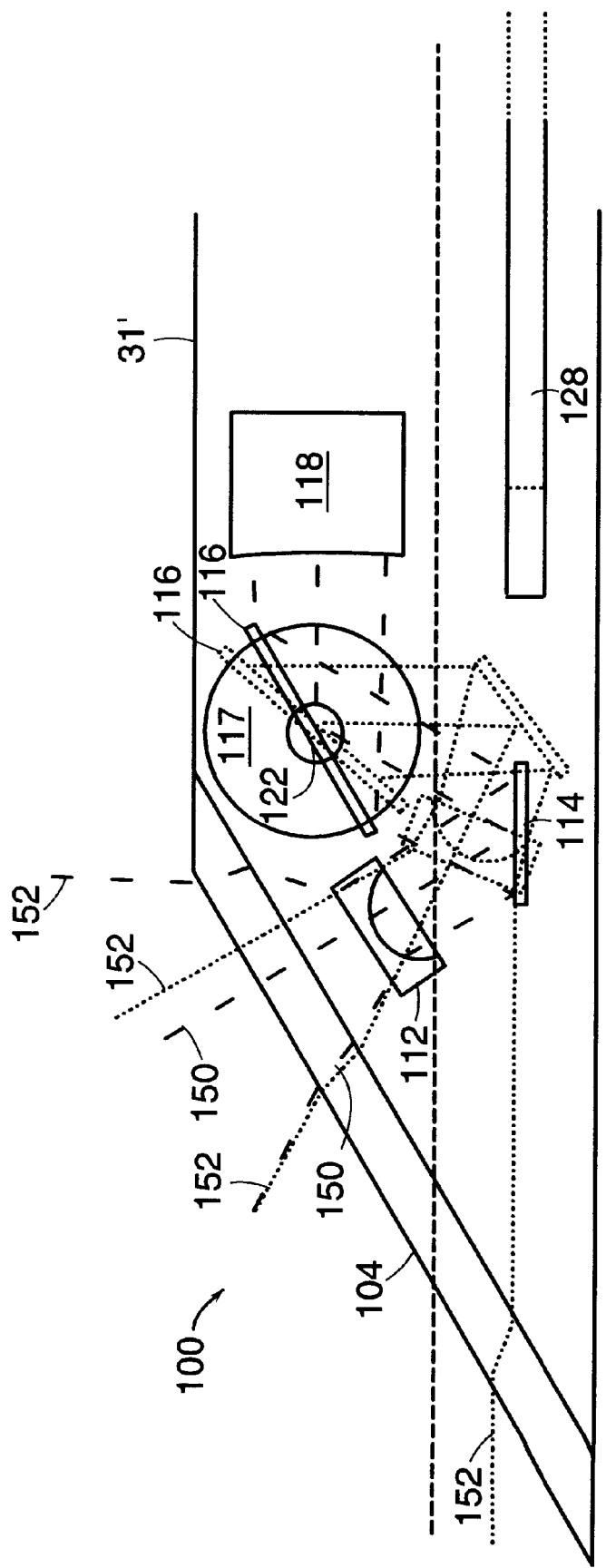
FIG. 16 is a sectional elevation view of the input end of a variable view arthroscope, showing the orientation of image rays in both a maximum upward view and a maximum downward view, in accordance with an embodiment of the present invention.

As the input lens assembly 120 rotates, the position of the second mirror 116 must change to preserve the desired alignment. Due to the geometry of mirrors, the angle change in a reflected ray will be double the angle change in the mirror, such as when the mirror rotates from a first position to a second position. Specifically, the angle change in a ray reflected from first mirror 114 will be double the angle change in the mirror 114 and input lens assembly 120. Because the input lens assembly 120 is fixed in relation to the axle 122, the axial ray reflecting from the first mirror 114 always extends to a point on the second mirror 116 along the axle 122. The axle 122 is a fixed distance from the first mirror 114 and so the distance between the centers of the two mirrors is preserved regardless of the view. In order for the axial ray to be reflected at the proper angle toward the center of the relay system 118, however, the second mirror 116 must rotate one half the angular change of the input lens assembly 120. Accordingly, as the input lens assembly 120 rotates, the second mirror 116 should preferably rotate, and preferably only half the angle that the input lens assembly 120 rotates. Referring to FIG. 16 for purposes of illustration, the first mirror has a first position m1a corresponding to a first view of the arthroscope 30' and a second position m1b (shown in broken lines) corresponding to a second view of the arthroscope. The second mirror has a first position m2a corresponding to a first view of the arthroscope and a second position m2b (shown in broken lines) corresponding to a second view of the arthroscope. For any two viewing positions, the angular difference between m1a and m1b should be twice the angular difference between m2a and m2b. In a preferred embodiment, if the input lens assembly 120 has a rotational range of about 30 degrees from a full-up view to a full-down view, the second mirror 116 correspondingly has a rotational range of about 15 degrees.

In a preferred embodiment, the rotation of the input lens assembly 120 and of the second mirror 116 is controlled by a single push rod 128. The push rod 128, analogous to control rod 45 discussed hereinabove, is controlled from the outer control portion 35, preferably by control knobs 49,50 in a manner and with a mechanism similar to that described in relation to other embodiments of the present invention. The push rod 128 effects different angles of rotation for the input lens assembly 120 and for the second mirror 116. The push rod 128 moves the mirrors 114, 116 by moving the swing arms 124, 126. For the angle change of the first mirror 114 to be twice the angle change of the second mirror 116, the length of the swing arm 124 connecting the first mirror 114 to the push rod 128 should be half the length of the swing arm 126 connecting the second mirror 116 to the push rod 128. As the two swing arms 124, 126 rotate about the axle 122 to sweep out equal arcs, the longer swing arm 126 will cover a smaller angle than the shorter swing arm 124. In a preferred embodiment, when the input lens assembly 120 is positioned in the middle view, the swing arms 124, 126 are vertical, that is, at 90 degrees to the axial ray as it passes between the second mirror 116 and the lens relay system 118, to establish the desired relationship between the position of the first mirror 114 and the second mirror 116. The 90 degree angle is created by a line between the center of axle 122 and the rotational points on swing arms 124, 126 at the connection point of connecting rods 134, 136 and the axial ray as it passes between the second mirror 116 and the lens relay system.

In the illustrated embodiment, each swing arm 124, 126 is connected to the push rod 128 with a connecting rod 134, 136. The connecting rods 134,136 allow the linear motion of the push rod 128 to be converted to the rotational motion of the swing arms 124, 126 and allow the swing arms 124,126 to rotate freely. The connecting rods 134, 136 move at both ends and are preferably attached to the push rod 128 and to the swing arms 124, 126 by pins or other fasteners, such as shoulder screws. It should be understood that any mechanical arrangement that preserves the desired geometries of the mirrors and input lens is suitable; for example, more than one push rod may be effective.

The object rays obtained through the input lens 112, first mirror 114, and second mirror 116 are preferably relayed to the outer control portion 35 of the arthroscope 30'. It is preferred that the rays be relayed so as to preserve the quality of the image and to minimize aberrations. A lens relay system 118 passes the object rays to the control end. In various embodiments, the lens relay system 118 is a lens or a series of lenses, one alternative of which is commonly referred to as a field and relay lens system. The lens relay system 118 is preferably coaxial with the point on the second mirror 116, preferably on the center line of the axle 122, where the axial object ray 150 is reflected. In alternative embodiments, the lens relay system 118 may be replaced by an optical fiber coherent bundle. In additional embodiments, the lens relay system 118 may be a graded index lens or other lens having a varying refractive index. Although lens relay system 118 is shown as being contained within the input end 100 of the housing tube 31', the lens relay system 118 typically extends further towards the control end 33. If lens relay system 118 is replaced with a coherent bundle of optical fibers or is replaced with a graded index lens system, each will typically extend substantially along the length of housing tube 31' as does lens relay system 118.

Figure 15A:
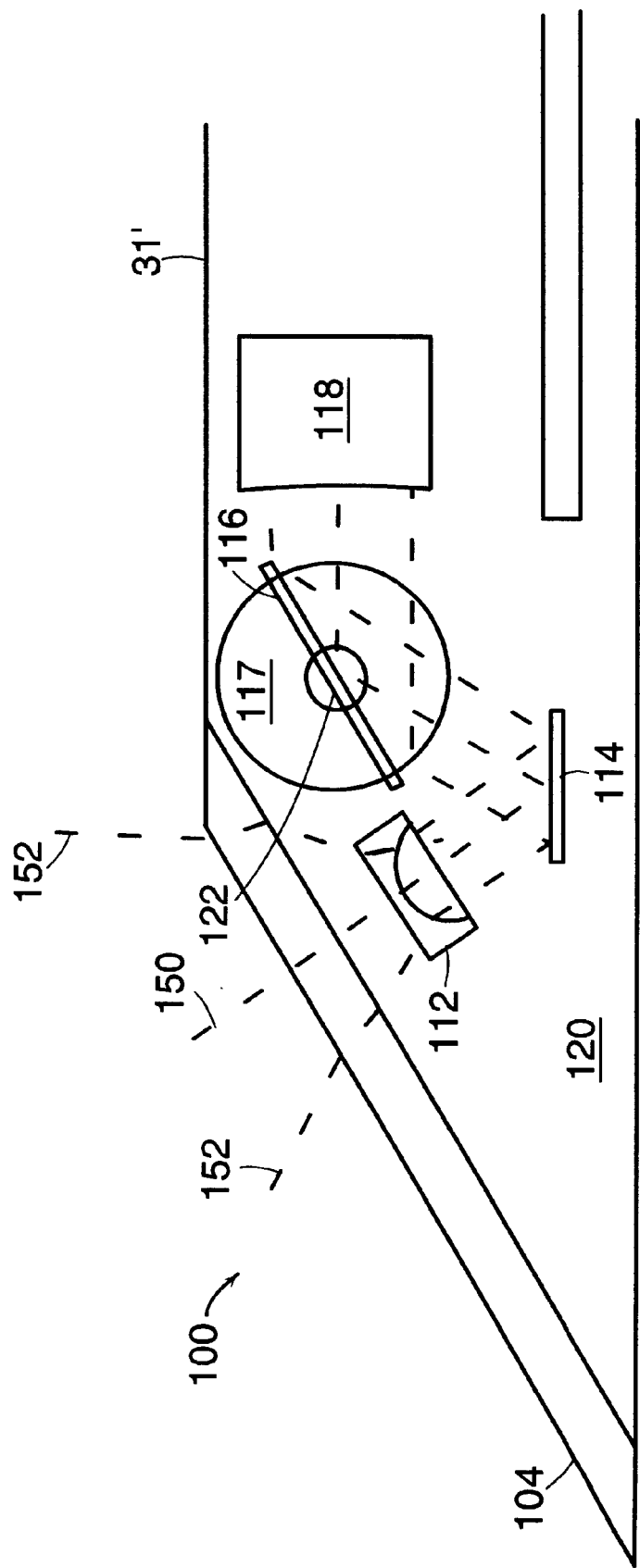
FIG. 15A is a sectional elevation view of the input end of a variable view arthroscope, showing the orientation of object rays in a maximum upward view in accordance with an embodiment of the present invention.
Figure 15B:
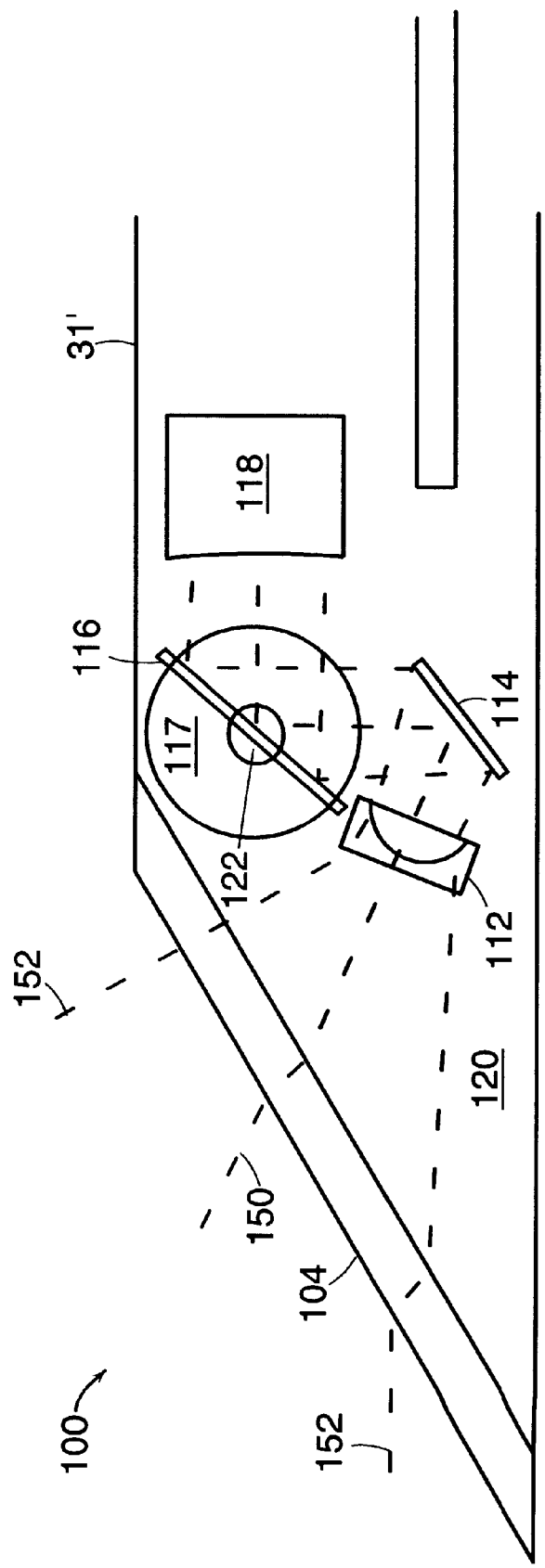
FIG. 15B is a sectional elevation view of the input end of a variable view arthroscope, showing the orientation of object rays in a maximum downward view, in accordance with an embodiment of the present invention.

In preferred embodiments of the present invention, the input lens 112, the first mirror 114 and the second mirror 116 are preferably arranged so as to preserve the various image ray path lengths when the view is altered, in order to preserve the focus of the image and minimize aberration. This feature can be better understood by reference to FIGS. 15 A–B and 16. The length of the axial ray 150 remains the same whether the view of the arthroscope 30' is at full-up (FIG. 15A) or full-down (FIG. 15B). Similarly, the lengths of the rim rays 152, typically the rays at the top and bottom of the image, are the same whether the view of the arthroscope 30' is at full-up (FIG. 15A) or full-down (FIG. 15B). The lengths of the rim rays 152 are also the same as each other. Once focused, all rays of the system stay in focus regardless of the view. In this system, the distortion created by a wide angle lens does not change regardless of view. This analysis is further illustrated in FIGS. 15A and 15B. FIG. 16 illustrates the image tracings for the full-up and full-down view superimposed in the same view. The path of the axial ray in the arthroscope 30' can be better understood by reference to this figure. The axial ray 150 passes through the center of the input lens 112, reflects from the center of the first mirror 114 and reflects at the center line of the axle 122 from second mirror 116 to the center of the first lens of the relay lens system 118. The path length of the axial ray 150 is always the same, regardless of the view of the arthroscope 30': the path length of the axial ray 150 is fixed (1) from the input lens 112 to the first mirror 114 because they are fixed with respect to each other; (2) from the first mirror 114 to the second mirror 116 because the center point of the surface of the second mirror 116 where the axial ray 150 will reflect is on the axle 122, which is the point about which the first mirror 112 rotates and is a fixed distance from the first mirror 112; (3) from the center of the second mirror 116 to the optical center of the first lens of the relay lens system 118, which is a constant distance from the center of the second mirror 118 fixed at the axle 122.

The language used herein is used for purposes of reference and not limitation. While the invention has been particularly shown and described with reference to preferred embodiments, it will be apparent to those skilled in the art that various modifications and alterations can be made in the device of the present invention without departing from the spirit and scope of the invention.

What is claimed is:

1. A variable view arthroscope with a plurality of viewing positions in a viewing range between a first end viewing position and a second end viewing position, comprising:
   a tubular housing having a longitudinal axis and an input end;
   a mirror axis transverse to the longitudinal axis;
   a first mirror in the housing at a distance from the minor axis; and
   a second mirror in the housing;
   the first mirror and the second mirror being rotatable relative to the housing about the mirror axis.

2. The variable view arthroscope of claim 1, wherein the first mirror and the second mirror are arranged so that for the plurality of viewing positions, object rays received at the input end reflect from the first mirror to the second mirror, and wherein the rotation of the first mirror about the mirror axis provides the plurality of viewing positions.

3. The variable view arthroscope of claim 2, further comprising an input lens, wherein the first mirror is fixed in relation to the input lens, the input lens being rotatable about the mirror axis with the first mirror.

4. The variable view arthroscope of claim 3, further comprising a first swing arm, the input lens and the first mirror being mounted on the first swing arm.

5. The variable view arthroscope of claim 4, wherein the first swing arm has a pivot point at the mirror axis.

6. The variable view arthroscope of claim 3, further comprising a meniscus lens closing the input end of the housing.

7. The variable view arthroscope of claim 3, wherein the input lens is an image expanding lens.

8. The variable view arthroscope of claim 3, wherein the input lens and the first mirror are arranged so that the object rays pass through the input lens to the fist mirror.

9. The variable view arthroscope of claim 8, further comprising a relay lens system.

10. The variable view arthroscope of claim 9, wherein second mirror and the relay lens system are arranged so that the object rays reflect from the second mirror into the relay lens system.

11. The variable view arthroscope of claim 10, wherein the length of a rim object ray from the input lens to the relay lens system is the same in the plurality of viewing positions.

12. The variable view arthroscope of claim 11, wherein the length of the two rim object rays from the input lens to the relay lens system is the same in the plurality of viewing positions.

13. The variable view arthroscope of claim 12, wherein the length of the two rim object rays is the same as each other in the plurality of viewing positions.

14. The variable view arthroscope of claim 2, wherein a first mirror angle change between a first of the plurality of viewing positions and a second of the plurality of viewing positions is twice as large as a second mirror angle change between the first and the second of the plurality of viewing positions for the plurality of viewing positions.

15. The variable view arthroscope of claim 1, wherein the mirror axis is coplanar with a reflecting surface of the second mirror.

16. The variable view arthroscope of claim 15, wherein the second mirror is a top-surface reflecting mirror.

17. The variable view arthroscope of claim 15, further comprising a relay lens system having an optical centerline parallel to the longitudinal axis, wherein object rays received at the input end reflect from the second mirror into the relay lens system along the optical centerline.

18. The variable view arthroscope of claim 1, wherein the fist mirror is rotatable by approximately 30 degrees between the first end viewing position and the second end viewing position.

19. The variable view arthroscope of claim 1, wherein the middle viewing position in the viewing range is at an angle about 45 degrees from the longitudinal axis.

20. The variable view arthroscope of claim 1, wherein the viewing range is greater than 100 degrees.

21. A variable view arthroscope with a plurality of viewing positions in a viewing range between a first end viewing position and a second end viewing position, comprising:
   a tubular housing having a longitudinal axis and an input end;
   a first mirror in the housing rotatable relative to the housing about a first mirror axis, the first mirror defining a first mirror angle change between a first of the plurality of viewing positions and a second of the plurality of viewing positions; and
   a second mirror in the housing rotatable relative to the housing about a second mirror axis, the second mirror defining a second mirror angle change between the first and the second of the plurality of viewing positions;
   wherein the first mirror angle change is twice as large as the second mirror angle change for the plurality of viewing positions.

22. The variable view arthroscope of claim 21, wherein the first or axis and the second mirror axis are a common mirror axis.

23. The variable view arthroscope of claim 22, further including a relay lens system, wherein the second mirror is oriented to reflect object rays received from the first mirror into the relay lens system.

24. The variable view arthroscope of claim 23, the relay lens system having an optical center, wherein the second mirror is oriented to reflect an axial object ray received from the first mirror to the optical center of the relay lens system.

25. The variable view arthroscope of claim 24, further comprising an input lens fixed in relation to the first mirror and rotatable about the common mirror axis with the first mirror, wherein the length of the two rim object rays from the input lens to the relay lens system is the same as each other in the plurality of viewing positions and is the same among the plurality of viewing positions.

26. A variable view arthroscope, comprising:

a first mirror, a first swing am having a distal end and a pivot end, the first mirror being mounted on the first swing arm proximate to the distal end;

an axle at the pivot end of the first swing arm, the axle having a central axis, the fist swing arm being rotatable about the axle;

a second mirror with a reflecting surface that is substantially coplanar with the central axis of the axle, the second mirror being rotatable about the axle.

27. The variable view arthroscope of claim 26, further comprising:

a housing tube, the housing tube having a longitudinal axis;

a second swing arm, the second swing arm having a mirror end and a connecting end, the second swing arm being connected to the second mirror at the mirror end;

a push rod, the push rod being parallel with and movable along the direction of the longitudinal axis;

a first connecting rod having a push rod end connected to the push rod and a swing arm end connected to the first swing arm; and a second connecting rod having a push rod end connected to the push rod and a swing arm end connected to the connecting end of the second swing arm;

wherein the distance between the swing arm end of the first connecting rod and the axle is approximately half the distance between the swing arm end of the second connecting rod and the axle.

28. The variable view arthroscope of claim 27, the arthroscope having a viewing range, wherein at the middle view in the viewing range, the first swing arm and the second swing arm are parallel.

29. The variable view arthroscope of claim 26, wherein for an angular rotation of the first mirror, the angular rotation of the second mirror is half as large.

* * * * *